United States Patent
Pastre et al.

(10) Patent No.: US 7,253,316 B2
(45) Date of Patent: *Aug. 7, 2007

(54) FLEXIBLE METHOD FOR THE JOINT PRODUCTION OF (I) FORMIC ACID, (II) A CARBOXYLIC ACID COMPRISING AT LEAST TWO CARBON ATOMS AND/OR THE DERIVATIVES THEREOF, AND (III) A CARBOXYLIC ACID ANHYDRIDE

(75) Inventors: Jörg Pastre, Bensheim (DE); Kai Michael Exner, Eppelheim (DE); Wolfram Stüer, Mannheim (DE); Elke Geissler, Ludwigshafen (DE); Otto Machhammer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 104 days.

This patent is subject to a terminal disclaimer.

(21) Appl. No.: 10/532,561

(22) PCT Filed: Oct. 21, 2003

(86) PCT No.: PCT/EP03/11622

§ 371 (c)(1),
(2), (4) Date: Apr. 25, 2005

(87) PCT Pub. No.: WO2004/037762

PCT Pub. Date: May 6, 2004

(65) Prior Publication Data

US 2006/0052631 A1    Mar. 9, 2006

(30) Foreign Application Priority Data

Oct. 26, 2002   (DE) ............................... 102 49 928

(51) Int. Cl.
*C07C 53/08*   (2006.01)
*C07C 53/00*   (2006.01)
*C07C 51/54*   (2006.01)

(52) U.S. Cl. .................. 562/609; 562/607; 562/893
(58) Field of Classification Search ............ 562/609, 562/606, 607, 887, 888, 895
See application file for complete search history.

(56) References Cited

U.S. PATENT DOCUMENTS 3,328,439 A    6/1967   Hamilton (Continued)

FOREIGN PATENT DOCUMENTS

DE        27 10 630 A1    3/1977

(Continued)

OTHER PUBLICATIONS

Ullmann's Encyclopedia of Industrial Chemistry 6th Edition, 2000 Electronic Release "Formic Acid".

(Continued)

*Primary Examiner*—Karl Puttlitz
(74) *Attorney, Agent, or Firm*—Connolly Bove Lodge & Hutz LLP

(57) ABSTRACT

Disclosed is a method for jointly producing (i) formic acid (III); (ii) a carboxylic acid comprising at least two carbon atoms (II) and/or the derivatives thereof; and (iii) a carboxylic acid anhydride (VII). According to said method, (a) a formic acid ester (I) is transesterfied to formic acid (III) and the corresponding carboxylic acid ester (IV) by means of a carboxylic acid comprising at least two carbon atoms (II); (b) at least one portion of the carboxylic acid ester (IV) formed in step (a) is carbonylated in order to obtain the carboxylic acid anhydride (V); and (c) at least one portion of the carboxylic acid anhydride (V) formed in step (b) is further dehydrated by means of a carboxylic acid (VI) so as to form a carboxylic acid anhydride (VII) and the carboxylic acid (II).

20 Claims, 4 Drawing Sheets

U.S. PATENT DOCUMENTS

| | | | |
|---|---|---|---|
| 4,002,678 A | 1/1977 | Naglieri et al. | |
| 4,239,698 A | 12/1980 | Isshiki et al. | |
| 4,333,885 A | 6/1982 | Feitler | |
| 4,374,070 A | 2/1983 | Larkins et al. | |
| 4,430,273 A | 2/1984 | Erpenbach et al. | |
| 4,519,956 A | 5/1985 | Lin et al. | |
| 4,559,183 A | 12/1985 | Hewlett | |
| 4,830,789 A | 5/1989 | Hinenoya et al. | |
| 4,959,498 A | 9/1990 | Luft et al. | |
| 5,003,104 A | 3/1991 | Paulik et al. | |
| 6,992,212 B2 * | 1/2006 | Zehner et al. | 560/234 |
| 2002/0161260 A1 | 10/2002 | Schmitt et al. | |

FOREIGN PATENT DOCUMENTS

| | | |
|---|---|---|
| DE | 28 36 084 A1 | 8/1978 |
| DE | 28 44 371 A1 | 10/1978 |
| DE | 35 06 632 A1 | 2/1985 |
| DE | 35 10035 A1 | 3/1985 |
| DE | 3644222 A1 | 12/1987 |
| EP | 0 004 641 A2 | 3/1979 |
| EP | 0 087 870 A1 | 7/1983 |
| EP | A-0 193 799 | 9/1986 |
| EP | 196520 * | 10/1986 |
| EP | A-0 196 520 | 10/1986 |
| EP | 0 231 689 A1 | 8/1987 |
| EP | 0 336 216 | 3/1989 |
| EP | 0 479 463 A2 | 4/1992 |
| EP | 0677 505 A1 | 10/1995 |
| EP | 1 231 201 A1 | 1/2002 |
| GB | 24 41 502 A1 | 8/1974 |
| GB | 2 333 773 A | 8/1999 |
| JP | 2135-445 A | 12/1985 |
| JP | 09124544 A | 10/1995 |
| SU | 1432048 A | 6/1986 |
| SU | 1432048 A1 | 6/1988 |
| WO | WO 82/01704 | 5/1982 |
| WO | WO 95/32940 | 12/1995 |

OTHER PUBLICATIONS

Ullmann's Encyclopedia of Industrial Chemistry 6$^{th}$ Edition, 2000 Electronic Release "Carboxylic Acids, Aliphatic".

Ullmann's Encyclopedia of Industrial Chemistry 6$^{th}$ Edition, 2000 Electronic Release "Esters, Organic".

Ullmann's Encyclopedia of Industrial Chemistry 6$^{th}$ Edition, 2000 Electronic Release "Acetic Acid".

Ullmann's Encyclopedia of Industrial Chemistry 6$^{th}$ Edition, 2000 Electronic Release "Acetic Anhydride and Mixed Fatty Acid Anhydrides".

Cd Römpp Chemie Lexikon- Version 1.0, Stuttgart/ NY: George Thieme Verlag 1995 "Säuereanhydride".

Ullmann's Encyclopedia of Industrial Chemistry 6$^{th}$ Edition, 2000 Electronic Release "Formic Acid"- Dervatives.

Ullmann's Encyclopedia of Industrial Chemistry 6$^{th}$ Edition, "Esters Organic".

Marr et al., The Carbonylation of Methylacetate to Acetic Anhydride Catalysed by [Cp*Rh(CO)$_2$] in the Absence of Hydrogen; Inorganic Chemistry Communications 3 (2000) pp. 617-619.

* cited by examiner

Fig. 1: Block diagram
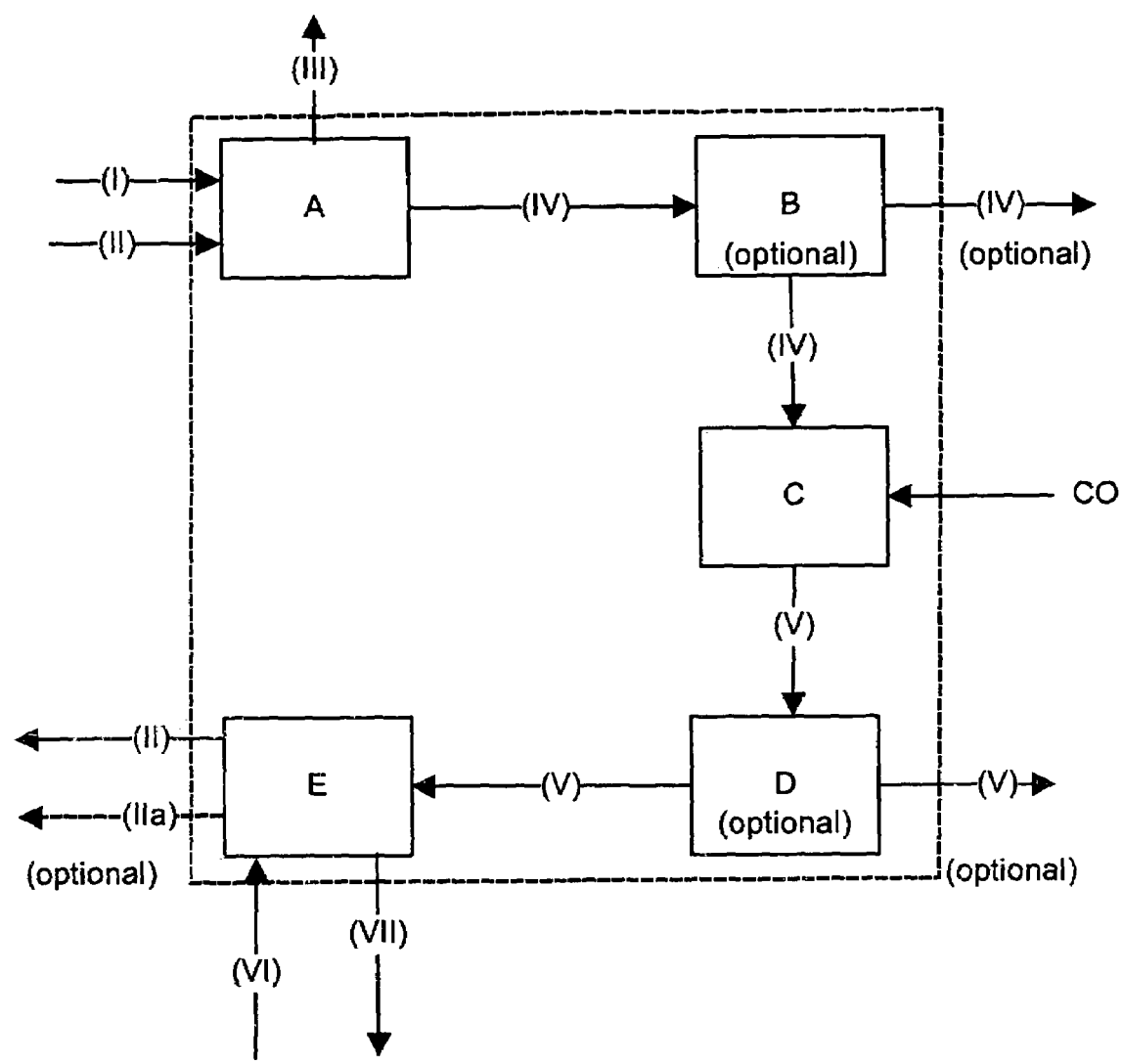

Fig. 2: Block diagram
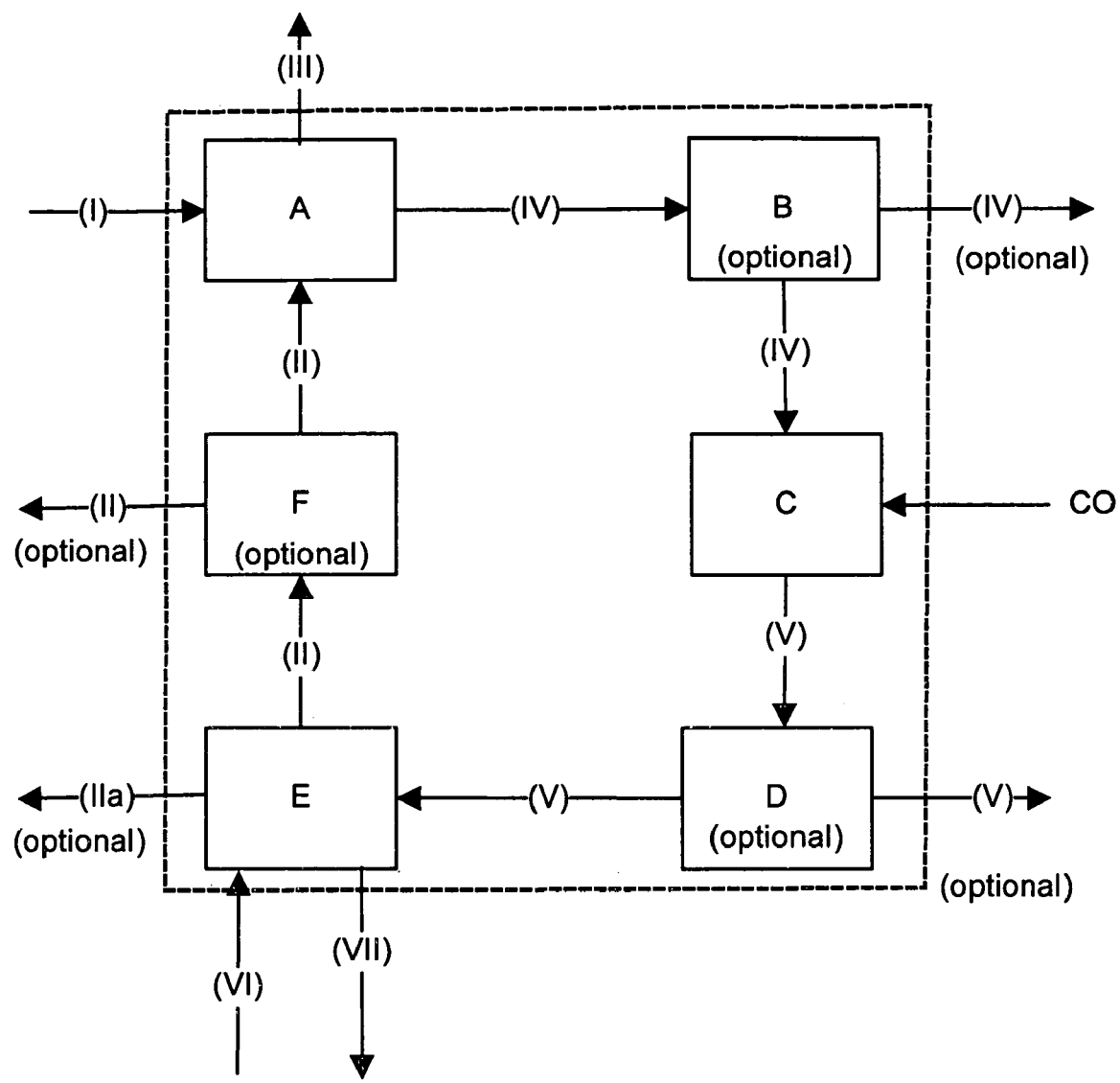

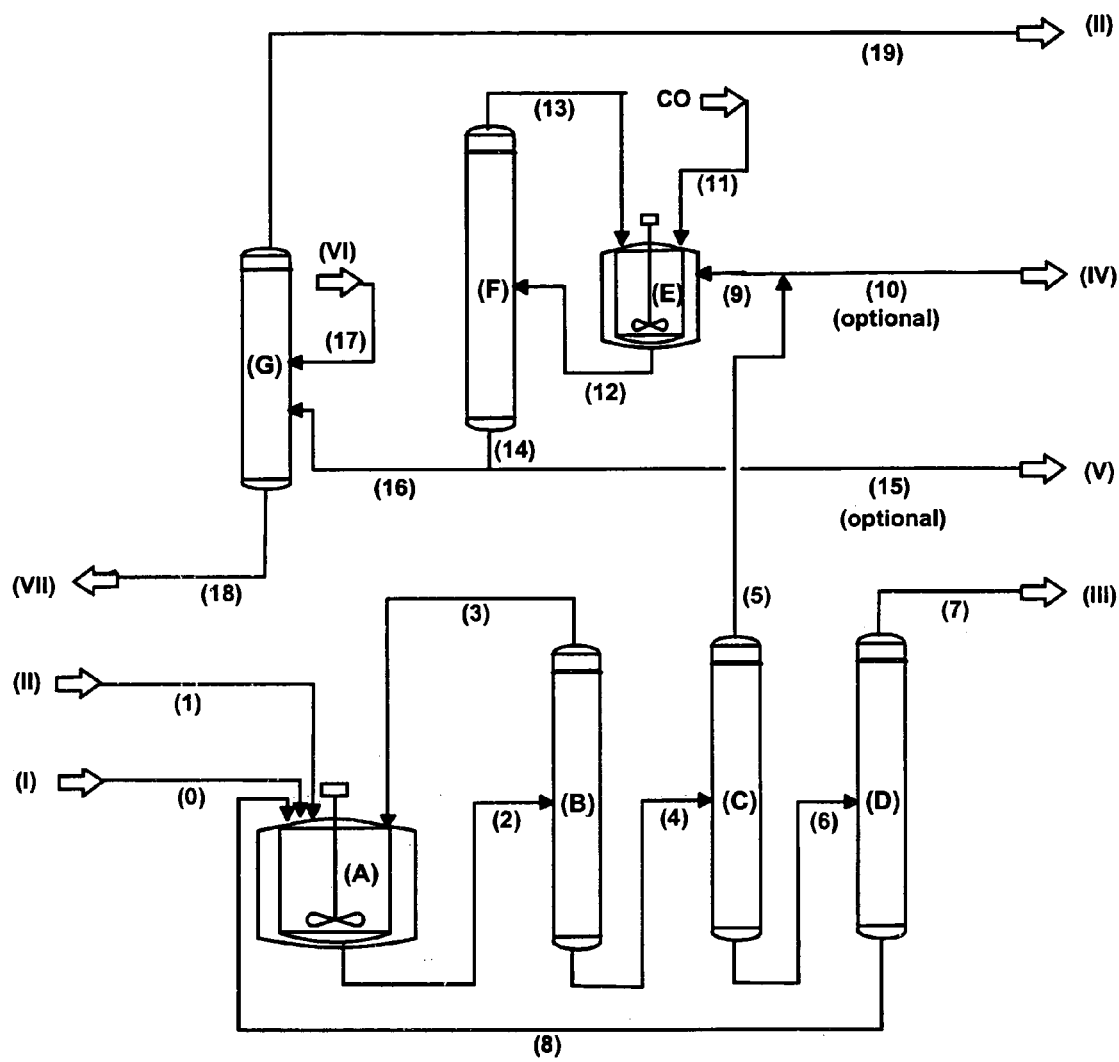
Fig. 3: Simplified process flow diagram for the preferred preparation of formic acid, carboxylic anhydride (VII) and acetic acid (Variant 1)

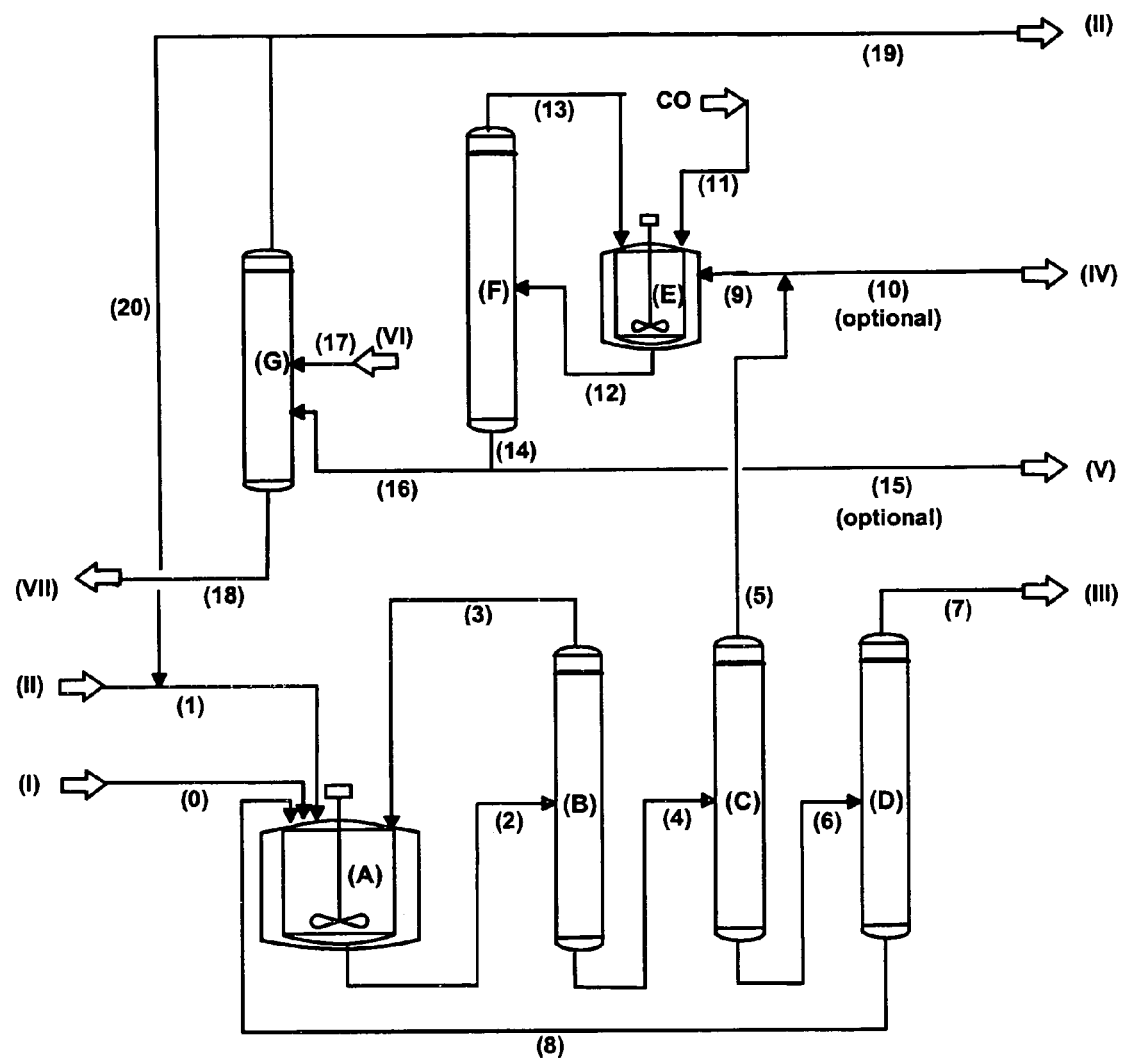
Fig. 4: Simplified process flow diagram for the preferred preparation of formic acid, carboxylic anhydride (VII) and acetic acid (with acetic acid circuit) (Variant 2)

FLEXIBLE METHOD FOR THE JOINT PRODUCTION OF (I) FORMIC ACID, (II) A CARBOXYLIC ACID COMPRISING AT LEAST TWO CARBON ATOMS AND/OR THE DERIVATIVES THEREOF, AND (III) A CARBOXYLIC ACID ANHYDRIDE

CROSS REFERENCE TO RELATED APPLICATION

The present application is a National Stage application of PCT/EP2003/011622, filed Oct. 21, 2003, which claims priority from German Patent Application No. DE 102 49 928.4, filed Oct. 26, 2002.

The present invention relates to a process for the joint preparation of (i) formic acid, (ii) a carboxylic acid having at least two carbon atoms and/or derivatives thereof, for example a carboxylic ester or a carboxylic anhydride, and (iii) a further carboxylic anhydride.

Formic acid is an important compound which has a wide variety of uses. It is used, for example, for acidification in the production of animal feed, as preservatives, as disinfectant, as auxiliary in the textile and leather industry and as synthetic building block in the chemical industry.

The most important processes for preparing formic acid are indicated below (cf. Ullmann's Encyclopedia of Industrial Chemistry, $6^{th}$ edition, 2000 electronic release, Chapter "FORMIC ACID—Production").

The industrially most important process for preparing formic acid is hydrolysis of methyl formate and subsequent concentration of the aqueous formic acid solution obtained. Known processes which may be mentioned are the Kemira-Leonard process and the BASF process. A great disadvantage of these processes is the formation of an aqueous formic acid solution as a result of the hydrolysis step, which results in a series of further disadvantages. Thus, complicated concentration of the formic acid solution by extractive rectification using an entrainer is required. As a result of the presence of water, the aqueous or concentrated formic acid solution to be handled is highly corrosive and requires the use of expensive materials of construction for the plant components concerned. The processes mentioned therefore suffer from high capital and operating costs, from a technically complicated and extensive construction of the production plant, a high energy consumption and a not inconsiderable residual water content in the concentrated formic acid.

The oxidation of hydrocarbons, for example butanes or naphtha, forms a broad range of products which includes formic acid and has to be separated and concentrated in a complicated manner. This process, too, suffers from the disadvantage of an extractive rectification of the crude formic acid using an entrainer being necessary. The abovementioned disadvantages resulting from the water content of are also present.

In an older process, formic acid is obtained by hydrolysis of formamide, which can be obtained by ammonolysis of methyl formate by means of ammonia. Hydrolysis is carried out using sulfuric acid and water. Disadvantages of this process are the undesirable formation of ammonium sulfate as coproduct and the presence of water, which leads to the abovementioned disadvantages.

Carboxylic acids such as acetic acid and its higher homologues and the corresponding anhydrides are important and versatile compounds. They are used, for example, for the preparation of esters, carboxylic anhydrides, as additives in the polymer sector or as intermediates in the preparation of textile chemicals, dyes, plastics, agrochemicals and pharmaceuticals. The low molcular weight homologues acetic acid and propionic acid are particularly important.

The most important processes for preparing acetic acid and its higher homologues are indicated below (cf. Ullmann's Encyclopedia of Industrial Chemistry, $6^{th}$ edition, 2000 electronic release, Chapter "ACETIC ACID—Production" and Chapter "CARBOXYLIC ACIDS, ALIPHATIC—Production").

The industrially most important process for preparing acetic acid is carbonylation of methanol in the presence of suitable carbonylation catalysts, for example cobalt carbonyl, iridium carbonyl or rhodium carbonyl compounds. Known processes which may be mentioned are the BASF process and the Monsanto process. A disadvantage of these processes is the presence of water in the reaction medium, which as a result of the water gas shift reaction of water and carbon monoxide to form carbon dioxide and hydrogen reduces the yield derived from the carbon monoxide used. Furthermore, a high energy input is necessary in the work-up by distillation because of the water content. In addition, the processes mentioned suffer from high capital and operating costs and require a technically complicated and extensive construction of the production plant.

The oxidation of hydrocarbons, for example ethane, butanes or naphtha, forms a broad range of products which comprise acetic acid and possibly higher homologues and have to be separated and concentrated in a complicated manner. The abovementioned disadvantages resulting from the water content also apply.

The synthesis of carboxylic acids by oxidation of the corresponding aldehydes starts out from expensive olefin as feedstock. Thus, acetaldehyde is prepared industrially by oxidation of ethene by the Wacker process and its higher homologues are obtained by hydroformylation of ethene, propene, etc. These processes therefore have an economically unattractive raw materials basis.

Carboxylic esters, in particular methyl acetate, are important solvents. Methyl acetate is used, for example, for dissolving nitrocellulose or acetylcellulose. Vinyl acetate is used widely in the preparation of polymers and copolymers.

There is a great variety of processes for preparing carboxylic esters (cf. Ullmann's Encyclopedia of Industrial Chemistry, $6^{th}$ edition, 2000 electronic release, Chapter "ESTERS, ORGANIC—Production"). Mention may be made of the esterification of carboxylic acids with alcohols, the reaction of carboxylic chlorides or carboxylic anhydrides with alcohols, the transesterification of carboxylic esters, the reaction of ketenes with alcohols, the carbonylation of olefins by means of carbon monoxide and alcohols, the condensation of aldehydes, the alcoholysis of nitriles and the oxidative acylation of olefins.

Alkyl acetates are obtained mainly by esterification of acetic acid or acetic anhydride with alkanols. Methyl acetate is also formed as by-product in the synthesis of acetic acid (cf. Ullmann's Encyclopedia of Industrial Chemistry, $6^{th}$ edition, 2000 electronic release, Chapter "ACETIC ACID—Production"). A further possible way of synthesizing methyl acetate is the carbonylation of dimethyl ether (cf. Ullmann's Encyclopedia of Industrial Chemistry, $6^{th}$ edition, 2000 electronic release, Chapter "ACETIC ANHYDRIDE AND MIXED FATTY ACID ANHYDRIDES—Acetic Anhydride—Production"). A disadvantage of the latter process is the use of expensive dimethyl ether.

Acetic anhydride is an important synthetic building block in the chemical industry and is used, for example, for preparing acetyl celluloses, acetylsalicylic acid, acetanilide, sulfonamides or vitamin B6.

The most important processes for preparing acetic anhydride are indicated below (cf. Ullmann's Encyclopedia of Industrial Chemistry, $6^{th}$ edition, 2000 electronic release, Chapter "ACETIC ANHYDRIDE AND MIXED FATTY ACID ANHYDRIDES—Acetic Anhydride—Production").

One industrially important process for preparing acetic anhydride is the reaction of acetic acid with ketene obtained in a previous step by thermal elimination of water from acetic acid. Disadvantages of this process are the very high energy consumption caused by the thermal preparation of ketene and the need to handle the extremely toxic ketene.

In a further industrially important process for preparing acetic anhydride, methanol is converted into methyl acetate by carbonylation and esterification in a first step and this is carbonylated in a second step to produce acetic anhydride.

A further process for preparing acetic anhydride is the liquid-phase oxidation of acetaldehyde. A disadvantage of this process is the use of expensive acetaldehyde which is obtained industrially by oxidation of ethene in the Wacker process. This process therefore has an economically unattractive raw materials basis.

A further process for preparing acetic anhydride is the carbonylation of methyl acetate in the presence of a transition metal catalyst. Methyl acetate is generally obtained as by-product in the synthesis of acetic acid and by esterification of acetic acid with methanol.

EP-A 0 087 870 teaches an integrated process for preparing acetic anhydride and acetic acid from methanol and carbon monoxide. In a first step, acetic acid is esterified with methanol to form methyl acetate which is carbonylated in the presence of water in a second step to give a mixture comprising acetic anhydride and acetic acid. The mixture obtained is worked up by distillation, with the required amount of acetic acid being fed to the first stage. The remaining amount of acetic acid and acetic anhydride is taken off as product. Disadvantages of this process are the formation of stoichiometric amounts of water in the esterification step and the associated problems occurring when handling water-containing acetic acid and in its work-up. The abovementioned disadvantages resulting from the water content apply.

Carboxylic anhydrides are important starting materials for other acid derivatives and are also used as solvents and as dehydrating agents. Anhydrides of unsaturated aliphatic carboxylic acids, in particular acrylic acid and methacrylic acid, are also important starting compounds for the preparation of interesting monomers which are difficult to obtain by other synthetic routes. Aromatic carboxylic anhydrides, for example 1,2,4,5-benzenetetracarboxylic dianhydride (pyromellitic anhydride) or 3,3',4,4'-benzophenonetetracarboxylic dianhydride, are important starting materials for the preparation of heat-resistant resins, for example polyamide or epoxy resins.

Various methods of preparing carboxylic anhydrides are known. An overview of the three principal synthetic routes may be found, for example, under the keyword "Säureanhydride" in CD Römpp Chemie Lexikon, Version 1.0, Stuttgart/New York Georg Thieme Verlag 1995. In the first synthetic route, the parent carboxylic acids are used and water is eliminated by use of water-withdrawing substances, for example $P_4O_{10}$, or by heating, thus forming the carboxylic anhydride. Disadvantages of this synthetic route are the use of starting materials whose preparation requires a great deal of energy (e.g. $P_4O_{10}$) and the formation of undesirable coproducts (e.g. phosphoric acid when $P_4O_{10}$ is used). A disadvantage of the thermal elimination of water is the risk of formation of undesirable by-products as a result of thermal decomposition. In the second synthetic route, acid chlorides, for example acetyl chloride or benzoyl chloride, are reacted with the alkali metal salts of the corresponding carboxylic acids. A process of this type is described, for example, in WO 95/32940. Disadvantages of this synthetic route are the use of an acid chloride which is a starting material whose preparation requires a great deal of energy and the formation of alkali metal chloride and the alkali metal salt of the acid chloride used as undesirable coproducts. In the third synthetic route, the parent carboxylic acids are transanhydrided with acetic anhydride or ketene. Details of this synthetic route are given, for example, in DE-A 35 10 035, EP-A 0 231 689, DE-A 36 44 222 and EP-A 1 231 201. A disadvantage of this synthetic route is the use of acetic anhydride or ketene which firstly have to be obtained by the energy-intensive process described above for acetic anhydride and ketene.

It is an object of the present invention to find a process for preparing carboxylic acids and/or derivatives thereof which no longer has the abovementioned disadvantages, has a readily available and economically attractive raw materials basis, makes a simple and inexpensive construction of the plant possible (low capital costs), avoids undesirable by-products as a result of coproduction and has a low energy consumption and favorable operating costs. A further object is to find a process which also makes it possible to prepare anhydrous carboxylic acids if required and thus makes the handling of less corrosive media and the use of less expensive materials of construction possible and as a result of the lower corrosivity also offers a higher degree of safety. Another object is to find a process which, quite generally, makes it possible to prepare a wide variety of carboxylic anhydrides, in particular unsaturated carboxylic anhydrides such as acrylic anhydride or methacrylic anhydride.

We have found that this object is achieved by a process for the joint preparation of
  (i) formic acid (III);
  (ii) a carboxylic acid having at least two carbon atoms (II) and/or derivatives thereof; and
  (iii) a carboxylic anhydride (VII), which comprises
  (a) transesterifying a formic ester (I) with a carboxylic acid having at least two carbon atoms (II) to form formic acid (III) and the corresponding carboxylic ester (IV);
  (b) carbonylating at least part of the carboxylic ester (IV) formed in step (a) to form the corresponding carboxylic anhydride (V); and
  (c) transanhydriding at least part of the carboxylic anhydride (V) formed in step (b) with a carboxylic acid (VI) to form a carboxylic anhydride (VII) and the carboxylic acid (II).

In step (a), a formic ester (I) is reacted with a carboxylic acid having at least two carbon atoms (II) to form formic acid (III) and the corresponding carboxylic ester (IV).

The formic ester used has the formula (I)

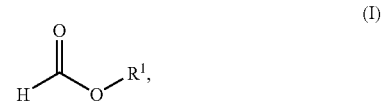

where the radical $R^1$ is an organic radical. The organic radical is preferably an unsubstituted or substituted, aliphatic, aromatic or araliphatic radical which has from 1 to 12 carbon atoms and may contain one or more heteroatoms such as oxygen, nitrogen or sulfur, for example —O—, —S—, —NR—, —CO— and/or —N= in aliphatic or aromatic systems, and/or be substituted by one or more functional groups which may contain, for example, oxygen, nitrogen, sulfur and/or halogen, for example by fluorine, chlorine, bromine, iodine and/or a cyano group.

Formic esters are generally obtainable by base-catalyzed carbonylation of the corresponding alcohols and by esterification of the corresponding alcohols with formic acid (cf. Ullmann's Encyclopedia of Industrial Chemistry, 6th edition, 2000 electronic release, Chapter "FORMIC ACID—Derivatives"). The simplest representative of this class of compounds, methyl formate, is obtained industrially by carbonylation of methanol.

BRIEF DESCRIPTION OF THE DRAWINGS

FIG. 1 shows a block diagram of the process of the present invention.
FIG. 2 shows a block diagram of the preferred process according to the present invention.
FIG. 3 shows a simplified process flow diagram.
FIG. 4 shows a simplified process flow diagram.

For the purposes of the present invention, a carboxylic acid having at least two carbon atoms (II) is a carboxylic acid which bears a radical having at least one carbon atom on the carboxyl group. The carboxylic acids used have the formula (II)

where the radical $R^2$ is an organic radical. The preferred organic radical $R^2$ is as defined in the case of $R^1$.

The abovementioned transesterification reaction in step (a) is an equilibrium reaction which is generally catalyzed by the presence of a catalyst.

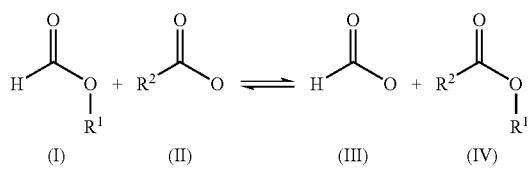

In the process of the present invention, step (a) can be carried out using known methods of transesterification (cf. Ullmann's Encyclopedia of Industrial Chemistry, 6th edition, 2000 electronic release, Chapter "ESTERS, ORGANIC—Chemical Properties" and "ESTERS, ORGANIC—Production" and the references below).

In general, small amounts of acidic or basic substances are used as catalyst. Preference is given to using acids and acidic solids. Examples which may be mentioned are strong protic acids, for example sulfuric acid, perchloric acid, benzenesulfonic acid, p-toluene sulfonic acid, molybdophosphoric acid and tungstosalicic acid; acidic ion exchangers, for example ion exchangers containing perfluorinated sulfonic acid groups (SU-A 1,432,048); and also acidic oxides, for example zeolites (DE-A 35 06 632), aluminosilicates (U.S. Pat. No. 3,328,439) or $SiO_2/TiO_2$ (DE 27 10 630). Preferred catalysts are mineral acids, p-toluenesulfonic acid and zeolites.

If strong protic acids are used as homogeneous catalysts, their concentration in the reaction mixture is generally from 0.01 to 50% by weight, preferably from 0.01 to 2% by weight.

As cocatalyst to be used together with the abovementioned catalysts, it is possible to use water or methanol, generally in an amount of up to 20% by weight, based on the reaction solution. However, it should be noted that an increase in the water content also increases the corrosivity of the reaction medium and makes the work-up of the products more difficult. It may therefore be advantageous to carry out the transesterification without addition of water or methanol as cocatalyst. If the transesterification is carried out in the presence of water or methanol, it may be advantageous to add carboxylic anhydride (V) to the reaction product mixture in order to bind the water. This can, for example, be added directly at the reactor outlet or in the column (e.g. bottom of the column). This measure also makes it possible to prepare anhydrous formic acid and an anhydrous carboxylic ester (IV) in a transesterification cocatalyzed by water or methanol. Anhydrous formic acid and anhydrous carboxylic ester (IV) can also be prepared without problems in this way when using methanol-containing methyl formate as formic ester (I). The typical residual methanol content of about 2–4% by weight when using methyl formate as formic ester (I) is found to be advantageous owing to its property as cocatalyst.

The transesterification can be carried out either in the liquid phase or in the gas phase. In the case of a transesterification in the gas phase, preference is given to using heterogeneous catalysts such as the abovementioned ion exchangers or acidic oxides. In a transesterification in the liquid phase, homogeneous or heterogeneous catalysts are used. The transesterification is preferably carried out in the liquid phase.

In general, the transesterification is carried out at from 20 to 300° C., preferably from 50 to 180° C.

The pressure is generally from 0.1 to 5 MPa abs.

The transesterification can be carried out in the presence of an additional inert, polar solvent. For the purposes of the present invention, inert solvents are solvents which do not react chemically with the starting materials, the products or the catalysts under the reaction conditions employed. Examples of suitable solvents are polyethers. Solvents are generally used in transesterifications in which starting materials and/or products which are insufficiently soluble in the solvent-free reaction mixture at the desired temperature, the desired pressure and the desired ratios of starting materials and products are present. If the starting materials and the products are also soluble in the solvent-free reaction mixture under the selected conditions, the transesterification is preferably carried out without addition of a solvent.

The starting materials formic ester (I) and carboxylic acid (II) are generally each added in the stoichiometric amount. Additional addition of one of the two starting materials, for example as an initial charge prior to the commencement of the reaction, enables a nonstoichiometric ratio of the two starting materials to be set in a targeted manner in the reaction mixture. In this way, for example, a starting material which has good solvent properties can improve the solubility of the other starting material or the product. It is likewise possible to maintain an appropriate excess of one of the two products in the reaction mixture.

The transesterification can be carried out batchwise or continuously. Preference is given to a continuous process.

In the process of the present invention, it is in principle possible to carry out the transesterification in any reaction apparatus known for transesterification reactions. Suitable reaction apparatuses for a reaction in the liquid phase are, for example, stirred tank reactors, distillation columns, reactive columns and membrane reactors. To achieve a high conversion, it is advantageous for at least one of the two products, preferably both, to be removed continually from the reaction mixture. When a stirred tank reactor is used, this is achieved, for example, by continuously taking off reaction mixture, subsequently separating the two products and recirculating the two unreacted starting materials and, if appropriate, the catalyst. When a distillation column is used, the transesterification reaction occurs in the liquid phase, with the lower-boiling components being able to be separated off by distillation and, depending on whether they are starting materials or product, recirculated or discharged. When a reactive column is used, the preferably heterogeneous catalyst is located in the separation region of the column. In a manner similar to the case of the distillation column described, the lower-boiling components are in this case separated off by distillation and recirculated or discharged.

Examples of suitable reaction apparatuses for a reaction in the gas phase are flow tubes or shaft reactors.

The separation of the reaction mixture can be carried out in various ways. The method is generally determined by the properties of the starting materials and products to be separated. Examples of possible separation methods are distillation, crystallization and extraction. It may be pointed out that combinations of various separation methods are also possible, including when a distillation column or reactive column has previously been used for the transesterification. In general, preference is given to separation by distillation, which can also be carried out under reduced pressure or in vacuo. If separation by distillation is not possible or possible only with great difficulty, for example in the case of relatively high-boiling or readily decomposable components, the alternative processes mentioned become important. A suitable work-up concept can be readily developed by a person skilled in the art from a knowledge of the starting materials, products and possibly the catalyst present.

Owing to its good distillation properties, formic acid (III) is preferably removed by distillation.

The preferred separation by distillation of the reaction mixture obtained is generally carried out using three distillation columns or their equivalents (e.g. a dividing wall column and a distillation column) to obtain a separation into four streams. The stream comprising the formic ester (I) is generally recirculated to the transesterification, the stream comprising the carboxylic ester (IV) is partly or entirely passed to the carbonylation step (b), the formic acid (III) is discharged from the system as product and the remaining stream comprising the carboxylic acid (II) is generally likewise recirculated to the transesterification.

Since any formic ester (I) still present is isomerized to the corresponding carboxylic acid $R^1$—COOH in the presence of the carbonylation catalyst in the subsequent carbonylation of the carboxylic ester (IV) to the carboxylic anhydride (V), it may be possible, in a variant with a simplified work-up by distillation saving a distillation column, to take off not only a stream comprising the formic ester (I), a stream comprising formic acid (III) and a stream comprising the carboxylic acid (II) but also a further stream comprising the formic ester (I) and the carboxylic ester (IV) and recirculate this to the carbonylation step (b). This latter stream can, for example, be obtained at a side offtake of the first distillation column.

In the process of the present invention, the total amount of the carboxylic ester (IV) obtained or only part thereof can be fed to the carbonylation step (b). In the latter variant, part of the carboxylic ester (IV) formed can be obtained as end product. The remaining part of the carboxylic ester (IV) is passed to the carbonylation step (b).

In step (b), at least part, preferably at least 5%, particularly preferably at least 10% and very particularly preferably at least 50%, of the carboxylic ester (IV) formed in step (a) is carbonylated in the presence of a catalyst to give the corresponding carboxylic anhydride (V).

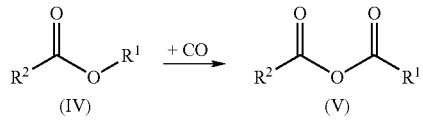

In the process of the present invention, step (b) can be carried out using known methods of carbonylating carboxylic esters (cf. Ullmann's Encyclopedia of Industrial Chemistry, 6$^{th}$ edition, 2000 electronic release, Chapter "ACETIC ANHYDRIDE AND MIXED FATTY ACID ANHYDRIDES—Acetic Anhydride—Production" and the references below).

As catalysts, it is generally possible to use metals of groups 8 to 10 of the Periodic Table and their compounds in the presence of halides and organic halogen compounds. Preferred catalyst metals are rhodium, iridium, palladium, nickel and cobalt, in particular rhodium (EP-A 0 677 505). As halides or organic halogen compounds, use is generally made of iodine compounds. Preference is given to adding alkali metal, iodides and alkaline earth metal iodides (U.S. Pat. No. 5,003,104, U.S. Pat. No. 4,559,183), hydrogen iodide, iodine, iodoalkanes, in particular iodomethane (methyl iodide) (GB-A 2,333,773, DE-A 24 41 502), or substituted azolium iodide (EP-A 0 479 463). The catalyst metals are generally stabilized by ligands. As ligands, preference is given to using nitrogen and phosphorus compounds such as N-containing heterocyclic compounds (DE-A 28 36 084), amines, amides (DE-A 28 44 371) or phosphines (U.S. Pat. No. 5,003,104, EP-A 0 336 216). The catalyst systems can further comprise promoter metals, for example chromium in the nickel/chromium system (U.S. Pat. No. 4,002,678), ruthenium in the iridium/ruthenium system (GB-A 2,333, 773) or cobalt in the ruthenium/cobalt system (U.S. Pat. No. 4,519,956). Preferred catalyst systems are systems comprising rhodium and/or iridium, methyl iodide, nitrogen- and/or phosphorus-containing ligands and, if desired, promoters, for example lithium or chromium. Particular preference is given to using a catalyst based on rhodium triiodide, lithium iodide and iodomethane, for example as described in U.S. Pat. No. 4,374,070.

The catalyst can be used in unsupported form as homogeneous catalyst or in supported form as heterogeneous catalyst. Suitable support materials are, for example, inorganic oxides such as silicon dioxide or aluminum oxide (EP-A 0 336 216), or polymers such as ion exchangers (J6 2135 445) or resins (JP 09 124 544).

The carbonylation can be carried out in the presence of hydrogen (U.S. Pat. No. 5,003,104, GB-A 2 333 773, U.S. Pat. No. 4,333,885, WO 82/01704) or in the absence of hydrogen (A. C. Marr et al., Inorg. Chem. Comm. 3, 2000, pages 617 to 619). It is generally advantageous to carry out the carbonylation in the presence of hydrogen, generally using hydrogen concentrations from the ppm range up to 15% by volume, preferably from 1 to 10% by volume, based on the gaseous feed stream employed.

The carbonylation can be carried out either in the gas phase (EP-A 0 336 216) or in the liquid phase. When it is carried out in the gas phase, use is generally made of supported catalysts. In the process of the present invention, preference is given to the carbonylation being carried out in the liquid phase.

The carbonylation in the gas phase is generally carried out at from 130 to 400° C., preferably from 150 to 280° C., and a pressure of from 0.1 to 15 MPa abs, preferably from 0.5 to 3 MPa abs. The carbonylation in the liquid phase is generally carried out at from 100 to 300° C., preferably from 170 to 200° C., and a pressure of from 0.1 to 15 MPa abs, preferably from 1 to 8 MPa abs.

When the carbonylation is, as preferred, carried out in the liquid phase and a homogeneous catalyst is used, the catalyst concentration employed is generally in the range from 0.01 to 1% by weight, based on the reaction solution.

The carbonylation can be carried out in the presence of an additional inert solvent. For the purposes of the present invention, inert solvents are solvents which do not react chemically with the starting compounds, the products or the catalysts under the reaction conditions employed. Suitable inert solvents are, for example, aromatic and aliphatic hydrocarbons and also carboxylic acids and their esters. Preference is given to using solvents in carbonylations in which the starting material and/or the product is insufficiently soluble in the solvent-free reaction mixture at the desired temperature and/or the desired pressure. If the starting materials and the products are also soluble in the solvent-free reaction mixture under the selected conditions, the transesterification is preferably carried out without addition of a solvent.

The carbonylation can be carried out batchwise or continuously. Preference is given to a continuous process.

In the process of the present invention, the carbonylation can in principle be carried out using any reaction apparatuses known for carbonylation reactions. The carbonylation in the gas phase is generally carried out in a flow tube or shaft reactor. Suitable reaction apparatuses for the preferred carbonylation in the liquid phase are, for example, stirred tank reactors, jet loop reactors and bubble columns. Their use in a continuous process is briefly described below.

When the abovementioned reaction apparatuses are used, the desired amounts of carboxylic ester (IV) and carbon monoxide are generally passed continuously into the reaction solution comprising, in particular, the carboxylic anhydride (V), the carbonylation catalyst and, if desired, an additional solvent with intensive mixing. The heat of carbonylation evolved can, for example, be removed by means of internal heat exchangers, by cooling the wall of the reaction apparatus and/or by continuously taking off the hot reaction solution, cooling it externally and recirculating it. When a jet loop reactor or a bubble column is used, an external circuit is necessary to ensure mixing. The product is taken off by continuously taking off reaction mixture and subsequently separating off the carbonylation catalyst in a suitable separation apparatus. A suitable separation apparatus is, for example, a flash evaporator in which the carboxylic anhydride (V) is vaporized by pressure reduction. The remaining solution, which comprises the carbonylation catalyst, is returned to the reaction apparatus. Under suitable temperature and pressure conditions, it may also be possible for the carboxylic anhydride formed to be taken off continuously from the reaction solution by vaporization (DE-A 30 24 353). The vaporized carboxylic anhydride (V) can, depending on requirements, be passed to a work-up step or a subsequent step for further reaction. In the case of relatively high-boiling carboxylic anhydrides (V) for which the flash evaporation described is not possible because of their low volatility, the reaction product mixture is worked up in other ways, for example by distillation under reduced pressure, by crystallization or by extraction.

The process parameters and measures to be chosen in the process of the present invention are dependent, inter alia, on the nature of the carboxylic ester (IV) used, the carboxylic anhydride (V) formed and the catalyst system selected and can be determined using customary technical skills.

Depending on the formic ester (I) and carboxylic acid (II) chosen as starting materials, the carbonylation in step (b) forms a symmetrical or unsymmetrical carboxylic anhydride, i.e. the radicals $R^1$ and $R^2$ can be identical or different.

Furthermore, it is possible to add an alcohol $R^1$—OH or $R^2$—OH to the carboxylic ester (IV) to be carbonylated. The alcohol is then converted into the corresponding carboxylic acid $R^1$—COOH or $R^2$—COOH (II). Such an addition makes it possible to increase the ratio of the carbonylation products $R^2$—COOH (II), carboxylic anhydride (V) and $R^1$—COOH to formic acid (I). Thus, for example, the additional introduction of methanol in the carbonylation of methyl acetate leads to formation of acetic acid in addition to acetic anhydride from the carbonylation of the methyl acetate. It is also possible to add water, carboxylic ester (IV), formic ester (I) or ethers of the formula $R^1$—O—$R^1$, $R^1$—O—$R^2$ or $R^2$—O—$R^2$ as further components to the carboxylic ester (IV) to be carbonylated.

In the process of the present invention, the entire amount of the carboxylic anhydride (V) obtained or only part thereof can be passed to the transanhydridation step (c). In the latter variant, part of the carboxylic anhydride (V) formed can be obtained as end product. The remaining part of the carboxylic anhydride (V) is passed to the transanhydridation step (c).

In step (c), at least part, preferably at least 5%, particularly preferably at least 10% and very particularly preferably at least 50%, of the carboxylic anhydride (V) formed in step (b) is transanhydrided by reaction with a carboxylic acid (VI).

The carboxylic acid to be used has the formula (VI)

where the radical $R^3$ is an organic radical. The organic radical is preferably an unsubstituted or substituted, aliphatic, aromatic or araliphatic radical which has from 1 to 12 carbon atoms and may contain one or more heteroatoms such as oxygen, nitrogen or sulfur, for example —O—, —S—, —NR—, —CO— and/or —N= in aliphatic or aromatic systems, and/or be substituted by one or more functional groups which may contain, for example, oxygen, nitrogen, sulfur and/or halogen, for example by fluorine, chlorine, bromine, iodine and/or a cyano group.

The abovementioned transanhydridation in step (c) is an equilibrium reaction. The starting materials carboxylic anhydride (V) and carboxylic acid (VI) are reacted according to the following reaction scheme to give the products carboxylic acid (II), carboxylic acid (IIa) and carboxylic anhydride (VII).

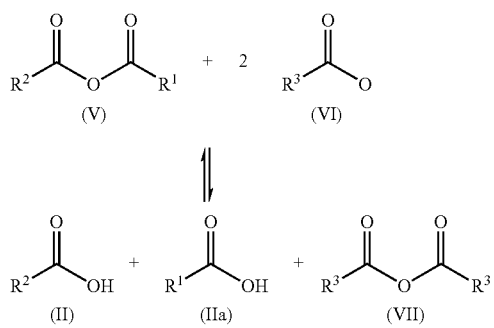

In the process of the present invention, step (c) can be carried out using known methods of transanhydridation. Suitable methods are described, for example, in DE-A 35 10 035, EP-A 0 231 689, DE-A 36 44 222 and EP-A 1 231 201.

To increase the reaction rate, it is generally advantageous to carry out the transanhydridation in the presence of catalysts. Suitable catalysts are, in particular, acidic or basic substances and also suitable metal ions.

If acidic substances are used as catalysts, they can in principle be solid, liquid or gaseous under the reaction conditions. Examples of suitable solid acidic or basic catalysts are acidic or basic ion exchangers and acidic or basic oxides,.for instance zeolites, aluminosilicates, $SiO_2/TiO_2$ or transition metal oxides. Suitable liquid or gaseous acidic catalysts include organic or inorganic acids which have a pKa which is lower than those of the carboxylic acid (VI) and the carboxylic acid (II). As organic or inorganic acids, preference is given to using sulfuric acid, aliphatic or aromatic sulfonic acids or phosphoric acid. The amount of organic or inorganic acid is advantageously from 0.01 to 2 mol %, preferably from 0.1 to 2 mol %, based on the carboxylic acid (VI) used.

If metal ions are used as catalysts, they are preferably metal ions of groups 1 to 13 of the Periodic Table. Preference is given to the ions of cobalt, chromium, nickel, manganese, iron, lithium, sodium, potassium, magnesium, barium, calcium, copper, zinc, zirconium, titanium, lanthanum, scandium, tungsten, cerium, molybdenum, thorium, yttrium, niobium, tantalum, hafnium, rhenium, aluminum and vanadium. The concentration of metal ions in the reaction mixture is advantageously from 5 to 1000 ppm by weight, preferably from 50 to 500 ppm by weight.

The transanhydridation can be carried out in the liquid phase or in the gas phase. In the case of a transanhydridation in the gas phase, preference is given to using heterogeneous catalysts, for example the abovementioned ion exchangers or acidic oxides. In the case of a transanhydridation in the liquid phase, catalysts used are preferably the abovementioned organic or inorganic acids or metal ions. The transanhydridation is preferably carried out in the liquid phase or in the liquid/gas phase.

The transanhydridation is generally carried out at from 20 to 300° C., preferably from 30 to 200° C. The pressure is generally from 0.001 to 5 MPa abs, preferably from 0.01 to 0.5 MPa abs.

The transanhydridation can be carried out in the presence of an additional inert, polar solvent. For the purposes of the present invention, inert solvents are solvents which do not react chemically with the starting materials, the products or the catalysts under the reaction conditions employed. Examples of suitable solvents are aromatic hydrocarbons and polyethers. Solvents are generally used in transanhydridations in which starting materials and/or products which are insufficiently soluble in the solvent-free reaction mixture at the desired temperature, the desired pressure and the desired ratios of starting materials and products are present. If the starting materials and products are also soluble in the solvent-free reaction mixture under the chosen conditions, the transanhydridation is preferably carried out without addition of a solvent.

The starting materials carboxylic anhydride (V) and carboxylic acid (VI) are generally added in the stoichiometrically required amounts. It may be advantageous to use an excess of carboxylic anhydride (V) to shift the equilibrium in the direction of the desired carboxylic anhydride (VII) and achieve a complete conversion, viewed externally, of the carboxylic acid (VI) used. This excess of carboxylic anhydride (V) is advantageously up to 0.5 mol per mol of carboxylic acid (VI).

The transanhydridation can be carried out batchwise or continuously. Preference is given to a continuous process with continuous introduction of the starting materials carboxylic anhydride (V) and carboxylic acid (VI) and with continuous discharge of the reaction mixture for further work-up or continuous discharge of the desired product carboxylic anhydride (VII) and also the carboxylic-acids (II) and (IIa) form and, if applicable, the excess carboxylic anhydride (V).

In the process of the present invention, the transanhydridation can in principle can be carried out using all reaction apparatuses known for transanhydridation reactions. Examples of suitable reaction apparatuses for the reaction in the liquid phase are stirred tank reactors, distillation columns reactive columns and membrane reactors. To achieve a high conversion, it is advantageous for at least one of the two products, preferably all products, i.e. the carboxylic anhydride (VII) and the carboxylic acids (II) and (IIa), to be removed continually from the reaction system.

When using a stirred tank reactor, this is achieved, for example, by continuously taking off the reaction mixture, subsequently separating off the products and recirculating the unreacted starting materials and, if appropriate, the catalyst. The subsequent separation is generally carried out using one or more distillation columns. It is possible to design a separation process suitable for the specific system with the aid of customary technical skills.

The transanhydridation reaction is preferably carried out in a distillation column or reactive column. A method suitable for the process of the present invention is described, for example, in DE-A 35 10 035. In the case of a transanhydridation in a distillation column or reactive column, the reaction preferably occurs in-the middle region of the column. The carboxylic anhydride (V) and the carboxylic acid (VI) are fed in from the side in the middle part of the column. In general and especially when using acetic anhydride as carboxylic anhydride (V), the carboxylic acids (II) and (IIa) formed, which when using acetic anhydride are identical and are both acetic acid, is the component boiling at the lowest temperature. It is therefore generally taken off continuously at the top. The carboxylic anhydride (VII) formed is generally the component-boiling at the highest temperature and is generally taken off continuously at the bottom. To make an appropriate reaction zone possible in the column, it is particularly advantageous to introduce the carboxylic anhydride (V) at a point below that at which the carboxylic acid (VI) is introduced, so that the reactants flow in countercurrent toward one another. Furthermore, the addition according to the countercurrent principle also leads to an increase in the conversion, since, for example, a high concentration of carboxylic anhydride (V) is present in the lower region of the column and, in combination with a rather low concentration of carboxylic acid (VI), shifts the equilibrium there in the direction of the desired product carboxylic anhydride (VII). However, it is also possible to introduce the carboxylic anhydride (V) and the carboxylic acid (VI) into the column together at one point. This may, for example, be advantageous when the two starting materials have identical or very similar boiling points. If a heterogeneous catalyst is used, it is preferably present in the form of fixed packing or coatings within the column interior. If homogeneous catalysts are used, these are fed into the column as further components, generally likewise continuously. Metal ions as homogeneous catalysts are generally introduced in the upper region of the column and discharged at the bottom, separated off from the bottom product and generally recirculated. Thus, for example, liquid acids which are discharged via the bottom product are preferably introduced in the upper region of the column. In a manner analogous to the description given for the use of metal ions, the organic or inorganic acids discharged with the bottoms are likewise separated off from the carboxylic anhydride (VII) and are generally recirculated. Organic or inorganic acids are generally introduced in the region at the opposite end of the column from the point at which they are taken off, so that they are distributed over the column. Thus, for example, relatively high-boiling organic or inorganic acids which, in accordance with the conditions prevailing in the column, are taken off at the bottom are preferably added in the upper region.

In accordance with the above discussion, it is particularly advantageous in the process of the present invention for the transanhydridation in step (c) to be carried out in a continuously operated distillation column and for the reaction products carboxylic acid (II) and carboxylic anhydride (VII) formed to be taken off continuously.

Suitable apparatuses for the reaction in the gas phase are, for example, flow tubes or shaft reactors.

Any further purification of the products obtained which may be necessary can be developed on the basis of a knowledge of the starting materials, products and, if applicable, the catalyst and using customary technical skills.

FIG. 1 shows a block diagram of the process of the present invention. Formic ester (I) and carboxylic acid (II) are reacted in block "A" (transesterification/separation) to form formic acid (III) and carboxylic ester (IV). The formic acid (III) separated off is discharged as end product. The carboxylic ester (IV) separated off is passed via an optional block "B" (discharge of carboxylic ester), in which part of the carboxylic ester (IV) formed may be discharged as end product, to block "C" (carbonylation). Carbon monoxide is introduced to form the carboxylic anhydride (V). The carboxylic anhydride (V) is passed via an optional block "D" (discharge of carboxylic anhydride), in which part of the carboxylic anhydride (V) formed may be discharged, as end product, to block "E" (transanhydridation). There, carboxylic acid (VI) is introduced to form carboxylic anhydride (VII) and carboxylic acid (II) and, when an unsymmetrical carboxylic anhydride (V) is used, also carboxylic acid (IIa), which are discharged as products.

In a preferred embodiment of the process of the present invention, at least part of the carboxylic acid (II) formed in step (c) is returned to step (a). It is particularly advantageous in the process of the present invention for the carboxylic acid (II) to be recirculated to step (a) in a total amount approximately equal to that necessary for maintaining the circulation there. To avoid accumulation of undesirable by-products, it may be advantageous to recirculate slightly less carboxylic acid (II) than necessary to step (a) and to make up the difference by addition of fresh carboxylic acid (II).

FIG. 2 shows a block diagram of the preferred process according to the present invention. The blocks "A" to "E" are as described for the block diagram of FIG. 1. The only difference in this preferred process is that the carboxylic acid (II) coming from block "E" (transanhydridation) is passed via an optional block "F" (discharge of carboxylic acid), in which part of the carboxylic acid (II) formed may be discharged as end product, to the block "A" (transesterification/separation).

In the process of the present invention, preference is given to using a formic ester (I)

in which the radical $R^1$ is an unsubstituted or substituted, unbranched or branched, acyclic or cyclic $C_1$–$C_{12}$-alkyl radical such as methyl, ethyl, 1-propyl, 2-propyl, 1-butyl, 2-butyl, 2-methyl-1-propyl, 2-methyl-2-propyl, 1-pentyl, 2-pentyl, 3-pentyl, 3-methyl-2-butyl, 2-methyl-2-butyl, hexyl, heptyl, 2-ethyl-1-pentyl, octyl, 2,4,4-trimethyl-1-pentyl, nonyl, 1,1-dimethyl-1-heptyl, decyl, undecyl, dodecyl, phenylmethyl, 2-phenylethyl, 3-phenylpropyl, cyclopentyl, cyclopentylmethyl, 2-cyclopentylethyl, 3-cyclopentylpropyl, cyclohexyl, cyclohexylmethyl, 2-cyclohexylethyl or 3-cyclohexylpropyl; or an unsubstituted or substituted, unbranched or branched, acyclic or cyclic $C_2$–$C_{12}$-alkenyl radical such as vinyl (ethenyl), 1-propenyl, 2-propenyl, 1-methylvinyl, 3-butenyl, cis-2-butenyl, trans-2-butenyl, cis-1-butenyl, trans-1-butenyl, pentenyl, hexenyl, heptenyl, octenyl, nonenyl, decenyl, 3-cyclopentenyl, 2-cyclohexenyl, 3-cyclohexenyl or 2,5-cyclohexadienyl.

Particular preference is given to using a formic ester (I) in which the radical $R^1$ is an unsubstituted, unbranched or branched, acyclic $C_1$–$C_6$-alkyl radical, specifically methyl, ethyl, 1-propyl, 2-propyl, 1-butyl, 2-butyl, 2-methyl-1-propyl, 2-methyl-2-propyl, 1-pentyl and 1-hexyl. Very particular preference is given to using methyl formate, ethyl formate, propyl formate or butyl formate, in particular methyl formate.

In the process of the present invention, preference is given to using a carboxylic acid (II)

in which the radical $R^2$ is an unsubstituted or substituted, unbranched or branched, acyclic or cyclic $C_1$–$C_{12}$-alkyl radical, such as methyl, ethyl, 1-propyl, 2-propyl, 1-butyl, 2-butyl, 2-methyl-1-propyl, 2-methyl-2-propyl, 1-pentyl, 2-pentyl, 3-pentyl, 3-methyl-2-butyl, 2-methyl-2-butyl, hexyl, heptyl, 2-ethyl-1-pentyl, octyl, 2,4,4-trimethyl-1-pentyl, nonyl, 1,1-dimethyl-1-heptyl, decyl, undecyl, dodecyl, phenylmethyl, 2-phenylethyl, 3-phenylpropyl, cyclopentyl, cyclopentylmethyl, 2-cyclopentylethyl, 3-cyclopentylpropyl, cyclohexyl, cyclohexylmethyl, 2-cyclohexylethyl, 3-cyclohexylpropyl, chloromethyl, dichloromethyl, trichloromethyl; or an unsubstituted or substituted, unbranched or branched, acyclic or cyclic $C_2$–$C_{12}$-alkenyl radical such as vinyl (ethenyl), 1-propenyl, 2-propenyl, 1-methylvinyl, 3-butenyl, cis-2-butenyl, trans-2-butenyl, cis-1-butenyl, trans-1-butenyl, pentenyl, hexenyl, heptenyl, octenyl, nonenyl, decenyl, 3-cyclopentenyl, 2-cyclohexenyl, 3-cyclohexenyl or 2,5-cyclohexadienyl.

Particular preference is given to using a carboxylic acid (II) in which the radical $R^2$ is an unsubstituted or substituted, unbranched or branched, acyclic $C_1$–$C_6$-alkyl radical, specifically methyl, ethyl, 1-propyl, 2-propyl, 1-butyl, 2-butyl, 2-methyl-1-propyl, 2-methyl-2-propyl, 1-pentyl, 2-pentyl, 3-pentyl, 3-methyl-2-butyl, 2-methyl-2-butyl, hexyl, chloromethyl, dichloromethyl or trichloromethyl; or an unsubstituted, unbranched or branched, acyclic $C_2$–$C_6$-alkenyl radical such as vinyl (ethenyl), 1-propenyl, 2-propenyl, 1-methylvinyl, 3-butenyl, cis-2-butenyl, trans-2-butenyl, cis-1-butenyl, trans-1-butenyl, pentenyl or hexenyl.

Very particular preference is given to using acetic acid and propionic acid, in particular acetic acid.

In the process of the present invention, preference is given to using a carboxylic acid (VI)

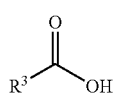

(VI)

in which the radical $R^3$ is an unsubstituted or substituted, unbranched or branched, acyclic or cyclic $C_2$–$C_{30}$-alkyl radical such as ethyl, 1-propyl, 2-propyl, 1-butyl, 2-butyl, 2-methyl-1-propyl, 2-methyl-2-propyl, 1-pentyl, 2-pentyl, 3-pentyl, 3-methyl-2-butyl, 2-methyl-2-butyl, hexyl, heptyl, 2-ethyl-1-pentyl, octyl, 2,4,4-trimethyl-1-pentyl, nonyl, 1,1-dimethyl-1-heptyl, decyl, undecyl, dodecyl, tridecyl, tetradecyl, pentadecyl, hexadecyl, heptadecyl, octadecyl, nonadecyl, eicosyl, henicosyl, docosyl, tricosyl, tetracosyl, pentacosyl, hexacosyl, heptacosyl octacosyl, nonacosyl, triacontyl, phenylmethyl, 2-phenylethyl, 3-phenylpropyl, cyclopentyl, 2-carboxycyclopentyl, cyclopentylmethyl, 2-cyclopentylethyl, 3-cyclopentylpropyl, cyclohexyl, 2-carboxycyclohexyl, cyclohexylmethyl, 2-cyclohexylethyl, 3-cyclohexylpropyl, chloromethyl, dichloromethyl or trichloromethyl;

an unsubstituted or substituted, unbranched or branched, acyclic or cyclic $C_2$–$C_{30}$-alkenyl radical, $C_2$–$C_{30}$-alkadienyl radical or $C_2$–$C_{30}$-alkatrienyl radical, for example vinyl (ethenyl), 1-propenyl, 2-propenyl, 1-methylvinyl, 3-butenyl, cis-2-butenyl, trans-2-butenyl, cis-1-butenyl, trans-1-butenyl, pentenyl, hexenyl, heptenyl, octenyl, nonenyl, decenyl, cis-8-heptadecenyl, trans-8-heptadecenyl, cis,cis-8,11-heptadecadienyl, cis, cis,cis-8,11,14-heptadecatrienyl, 3-cyclopentenyl, 2-cyclohexenyl, 3-cyclohexenyl or 2,5-cyclohexadienyl;

an unsubstituted $C_6$–$C_{20}$-aryl or $C_3$–$C_{20}$-heteroaryl radical or a $C_6$–$C_{20}$-aryl or $C_3$–$C_{20}$-heteroaryl radical substituted by one or more $C_1$–$C_4$-alkyl radicals, for example phenyl, 2-carboxyphenyl, 2,4,5-tricarboxyphenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl, 2-methoxyphenyl, 3-methoxyphenyl, 4-methoxyphenyl, 1-naphthyl, 2-napthyl, 2-carboxy-1-napthyl, 3-carboxy-2-naphthyl, 3,6,7-tricarboxy-2-naphthyl, 8-carboxy-1-naphthyl, 4,5,8-tricarboxy-1-naphthyl, 2-carboxy-1-anthracenyl, 3-carboxy-2-anthracenyl, 3,6,7-tricarboxy-2-anthracenyl, 4,9,10-tricarboxy-3-perylenyl or 4,3',4',-tricarboxy-3-benzophenonyl.

The carboxylic acid (VI) used is particularly preferably propionic acid, butyric acid, pentanoic acid, hexanoic acid, 2-ethylhexanoic acid, acrylic acid, methacrylic acid, phthalic acid, benzene-1,2,4,5-tetracarboxylic acid (pyromellitic acid), benzophenone-3,3',4,4'-tetracarboxylic acid, naphthalene-2,3,6,7-tetracarboxylic acid or naphthalene-1,4,5,8-tetracarboxylic acid.

The carboxylic anhydride (VII) prepared in the process of the present invention is particularly preferably propionic anhydride, butyric anhydride, acrylic anhydride, methacrylic anhydride and/or benzene-1,2,4,5-tetracarboxylic dianhydride (pyromellitic anhydride).

The process of the present invention is particularly preferably used to prepare (i) formic acid (III);

(ii) acetic acid, methyl acetate and/or acetic anhydride as carboxylic acid having at least two carbon atoms (II) and/or derivatives thereof; and (iii) propionic anhydride, butyric anhydride, acrylic anhydride, methacrylic anhydride and/or benzene-1,2,4,5-tetracarboxylic dianhydride (pyromellitic anhydride) as carboxylic anhydride (VII).

In the process of the present invention, the formic ester (I) and the carboxylic acid (II) are generally used in the transesterification in step (a) in a ratio of 1:1, although the relative concentrations in the reaction mixture may deviate therefrom. The carboxylic acid (II) is fed in as starting material, as recycle stream from step (c) or as a mixture of the two. Reaction of one mol of formic ester (I) and one mol of carboxylic acid (II) forms, in accordance with the reaction equation

one mol of formic acid (III) as product to be taken off and one mol of carboxylic ester (IV). Since at least part of the carboxylic ester (IV) formed in step (a) is carbonylated to the corresponding carboxylic anhydride (V), one mol of carboxylic anhydride (V) is formed from one mol of carboxylic ester (IV) in accordance with the reaction equation

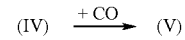

Since at least part of the carboxylic anhydride (V) formed in step (b) is used in the transanhydridation with introduction of the carboxylic acid (VI), one mol of carboxylic anhydride (VII), one mol of carboxylic acid (II) and one mol of carboxylic acid (IIa) are formed from one mol of carboxylic anhydride (V) and two mol of carboxylic acid (VI) in accordance with the reaction equation

$$(V) + 2\,(VI) \longrightarrow (VII) + (II) + (IIa)$$

If a symmetrical carboxylic anhydride (V) is used, two mol of carboxylic acid (II) are formed since the carboxylic acids (II) and (IIa) are then identical. The carboxylic acid (II) formed can be taken off as product or recirculated to the transesterification in step (a).

Table 1 gives an overview of the preferred process variants and indicates the stoichiometric ratios using the formic acid (III) formed as reference parameter. The last column indicates the process blocks required, with the optional blocks for discharge of possible intermediate products not being mentioned in the interests of simplicity.

Variant 1: Preparation of Formic Acid, Carboxylic Anhydride (VII) and Acetic Acid A simplified process flow diagram is shown in FIG. 3. Methyl formate (I) and acetic acid (II) are fed continuously via lines (0) and (1) into the reactor (A), which is depicted by way of example as a stirred vessel. However, other suitable reaction apparatuses such as those described above for step (a) can also be used as reactor (A). In, the reactor (A), the transesterification to form formic acid (III) and methyl acetate (IV) takes place in the presence of the catalyst used. The reaction mixture, which comprises methyl formate (I), acetic acid (II), formic acid (III), methyl acetate (IV) and the catalyst used, is taken continuously from the reactor (A) and passed via line (2) to the work-up by distillation, which is shown by way of example in the form of the columns (B), (C) and (D). Unreacted methyl formate (I) and any low boilers formed are recirculated via line (3) to the reactor (A). Formic acid (III) is taken off via line (7). Unreacted acetic acid (II), catalyst and any high boilers formed are recirculated to the reactor (A) via line (8). It goes without saying that part of the stream (8) can, if necessary, be discharged continuously or discontinuously to avoid accumulation of high boilers and, if desired, be worked up further. Methyl acetate (IV) is passed on via line (5). It is generally advantageous to use a dividing wall column for the two columns (B) and (C). In this case, stream (3) is taken off at the top, stream (5) is taken off as side stream and stream (6) is taken off at the bottom.

If desired, methyl acetate (IV) can be discharged via the optional line (10).

Methyl acetate (IV) is conveyed via line (9) to the carbonylation in reactor (E), which is depicted by way of example as a stirred vessel. However, other suitable reaction apparatuses, for example those described above for step (b), can also be used as reactor (E). In the reactor (E), carbonylation by means of carbon monoxide introduced via line (11) takes place in the presence of the catalyst used to form acetic anhydride (V). The reaction mixture, which comprises unreacted methyl acetate (IV), acetic anhydride (V) and the catalyst used, is taken continuously from the reactor (E), generally freed of the catalyst, for example in a flash evaporator (not shown in the interests of simplicity), and passed via line (12) to the work-up by distillation, which is shown by way of example in the form of the column (F). Unreacted methyl acetate (IV) and any low boilers formed are recirculated to the reactor (E) via line (13). The bottom product from the column (F), which comprises acetic anhydride (V) and any high boilers formed, is taken off via line (14) and is generally separated in a further column (not shown in the interests of simplicity) into acetic anhydride (V) and high boilers. The catalyst-containing stream is generally returned to the reactor (E). It goes without saying that part of the stream comprising high boilers can, if necessary, be discharged continuously or discontinuously to avoid accumulation of high boilers and, if desired, be worked up further.

If desired, acetic anhydride (V) can be discharged via the optional line (15).

Acetic anhydride (V) is conveyed continuously via line (16) to the transanhydridation in the reactor (G), which is depicted by way of example as a column. In the column (G), the carboxylic acid (VI) is introduced via line (17) and transanhydridation takes place in the presence of the catalyst used to form the carboxylic anhydride (VII) and acetic acid (II). The product from the top of the column (G), which comprises acetic acid (II), unreacted acetic anhydride (V) and any low boilers formed, is taken off via line (19) and generally fractionated further in a further column (not shown in the interest of simplicity). Acetic acid (II) is taken off as product, acetic anhydride (V) is generally returned to the column (G) and the low boilers are discharged. As an alternative, it is naturally also possible to hydrolyze any acetic anhydride (V) present in the product from the top of the column (G) by means of water to form acetic acid. The product from the bottom of the column (G), which comprises carboxylic anhydride (VII) and possibly the catalyst and high boilers formed, is taken off via line (18) and is generally separated in a further column (not shown in the interest of simplicity) into carboxylic anhydride (V), catalyst and high boilers. The catalyst-containing stream is generally recirculated to the column (G) and the carboxylic anhydride (V) is discharged as product.

As an alternative, it is also possible to use a series arrangement of a reactor, for example a stirred vessel, and one or more distillation columns connected in series for the work-up of the reaction mixture in place of the column (G) for the transanhydridation.

Variant 2: Preparation of Formic Acid, Carboxylic Anhydride (VII) and Acetic Acid (With Acetic Acid Circuit)

A simplified process flow diagram is shown in FIG. 4. The acetic acid (II) fed into the reactor (A) via line (20) comes predominantly, preferably entirely, from the acetic acid circuit. However, addition of additional acetic acid via line (1) is also possible if necessary. The transesterification, the carbonylation and the transanhydridation are carried out as described in variant 1, which is explicitly incorporated by reference at this point.

Instead of discharging all of the acetic acid (II) formed in the transanhydridation as product via line (19), in this preferred embodiment the acetic acid (II) necessary for the transesterification in step (a) is conveyed via line (20) back to the reactor (A), thus closing the circuit. Excess acetic acid (II) can naturally be taken off as product via line (19).

Variant 3: Preparation of Formic Acid, Carboxylic Anhydride (VII) and Acetic Anhydride (With Acetic Acid Circuit)

The likewise preferred variant 3 corresponds essentially to variant 2, except that part of the acetic anhydride (V) formed is discharged as product via line (15) and only the proportion necessary to maintain the acetic acid circuit is passed on to the transanhydridation. Thus, all of the acetic acid formed in the transanhydridation is recirculated via line (20) to the transesterification in this variant.

The process of the present invention makes it possible to prepare (i) formic acid, (ii) a carboxylic acid having at least two carbon atoms and/or derivatives thereof, for example a carboxylic ester or a carboxylic anhydride, and (iii) a further carboxylic anhydride on the basis of readily available and economically attractive raw materials. Thus, for example, the particularly preferred products formic acid, methyl acetate, acetic anhydride and acetic acid are based entirely on synthesis gas and thus on natural gas as raw material.

Furthermore, the process of the present invention makes possible a simple and inexpensive construction of the plant (low capital costs), a low energy consumption and low operating costs. Due to the coupling of the preparation of formic acid and a carboxylic acid having at least two carbon atoms and/or derivatives thereof, a plant operating according to the process of the present invention requires a significantly lower capital investment than two separate plants according to the prior art. In particular, the two separate plants according to the prior art are dispensed with. Furthermore, the circuit route via toxic ketene which requires a great deal of energy for its preparation is dispensed with in the preparation of acetic anhydride by the process of the present invention.

The process of the present invention avoids the formation of undesirable by-products as a result of coupled production.

Furthermore, the process of the present invention also makes it possible, if required, to prepare anhydrous formic acid and anhydrous carboxylic acids which are significantly less corrosive than the water-containing compounds and thus offer increased safety and allow the use of cheaper materials of construction. As a result of the simple (compared to the prior art) and economically attractive route to virtually anhydrous formic acid, a particularly high formic acid quality is achieved. The very low residual water content also results in an advantage in transport and storage of the formic acid prepared in this way.

Furthermore, the process of the present invention offers a high degree of flexibility in terms of the carboxylic acid having at least two carbon atoms and/or derivatives thereof, since the relative amounts of the compounds discharged can be varied within a wide range according to requirements. Additional introduction of an alcohol into the carbonylation step enables the ratio of the carbonylation products to formic acid to be increased. Thus, there is also a high degree of flexibility in respect of increased production of carbonylation products and their downstream products.

In the preferred preparation of acetic acid and its derivatives, the process of the present invention offers the further advantage of being able to carry out the carbonylation of methyl acetate in the absence of water and thus achieve a higher yield from the carbon monoxide used compared to the industrially customary carbonylation of methanol by avoiding the water gas shift reaction.

As a result of the use of the acetic anhydride prepared in a particularly advantageous manner as anhydride formation reagent for carboxylic acids, in particular propionic acid, butyric acid, acrylic acid and methacrylic acid, and the recirculation of the acetic acid formed to the acetic acid circuit, the preparation of a wide variety of carboxylic anhydrides from the parent carboxylic acids is also particularly advantageous.

TABLE 1

Preferred embodiments with indication of the idealized stoichiometric ratios

| | Starting materials | Products | Process blocks |
|---|---|---|---|
| 1 | (I): Methyl formate<br>(II): Acetic acid<br>Carbon monoxide<br>(VI): 2 carboxylic acid | (III): Formic acid<br>(II): 2 acetic acid<br>(VII): Carboxylic anhydride | A, C, E |
| 2 | (I): Methyl formate<br>Carbon monoxide<br>(VI): 2 carboxylic acid | (III): Formic acid<br>(II): Acetic acid<br>(VII): Carboxylic anhydride | A, C, E, F<br>Acetic acid (II) in circuit |
| 3 | (I): Methyl formate<br>Carbon monoxide<br>(VI): Carboxylic acid | (III): Formic acid<br>(II): ½ Acetic anhydride<br>(VII): ½ Carboxylic anhydride | A, C, D, E<br>Acetic acid (II) in circuit |

We claim:

1. A process for the joint preparation of
   (i) formic acid (III);
   (ii) a carboxylic acid having at least two carbon atoms (II) and/or derivatives thereof; and
   (iii) a carboxylic anhydride (VII);
   said process comprising:
   (a) transesterifying a formic ester (I) with a carboxylic acid having at least two carbon atoms (II) to form formic acid (III) and the corresponding carboxylic ester (IV);
   (b) carbonylating at least part of the carboxylic ester (IV) formed in step (a) to form the corresponding carboxylic anhydride (V); and
   (c) transanhydriding at least part of the carboxylic anhydride (V) formed in step (b) with a carboxylic acid (VI) to form a carboxylic anhydride (VII) and the carboxylic acid (II).

2. The process according to claim 1, wherein
   (d) at least part of the carboxylic acid (II) formed in step (c) is recirculated to step (a).

3. The process according to claim 1, wherein the transanhydridation in step (c) is carried out in the presence of an acidic or basic ion exchanger or an acidic or basic oxide.

4. The process according to claim 1, wherein the transanhydridation in step (c) is carried out in the presence of an organic or inorganic acid which has a $pK_a$ which is lower than that of the carboxylic acid (VI) and the carboxylic acid (II).

5. The process according to claim 1, wherein the transanhydridation in step (c) is carried out in the presence of a metal ion from groups 1 to 13 of the Periodic Table.

6. The process according to claim 1, wherein the transanhydridation in step (c) is carried out in a continuously operated distillation column and the reaction products carboxylic acid (II) and carboxylic anhydride (VII) formed are continuously taken off.

7. The process according to claim 1, wherein the formic ester (I) used is methyl formate.

8. The process according to claim 1, wherein the carboxylic acid (II) used is acetic acid.

9. The process according to claim 1, wherein the carboxylic anhydride (VII) prepared is at least one carboxylic anhydride (VII) selected from the group consisting of propionic anhydride, butyric anhydride, acrylic anhydride, methacrylic anhydride and benzene-1,2,4,5-tetracarboxylic dianhydride.

10. The process according to claim 1, wherein
(i) formic acid (III) is prepared;
(ii) the carboxylic acid having at least two carbon atoms (II) and derivatives thereof prepared is at least one carboxylic acid selected from the group consisting of acetic acid, methyl acetate and acetic anhydride; and
(iii) the carboxylic anhydride (VII) prepared is at least one carboxylic anhydride (VII) selected from the group consisting of propionic anhydride, butyric anhydride, acrylic anhydride, methacrylic anhydride and benzene-1,2,4,5-tetracarboxylic dianhydride.

11. The process according to claim 2, wherein the transanhydridation in step (c) is carried out in the presence of an acidic or basic ion exchanger or an acidic or basic oxide.

12. The process according to claim 2, wherein the transanhydridation in step (c) is carried out in the presence of an organic or inorganic acid which has a $pK_a$ which is lower than that of the carboxylic acid (VI) and the carboxylic acid (II).

13. The process according to claim 2, wherein the transanhydridation in step (c) is carried out in the presence of a metal ion from groups 1 to 13 of the Periodic Table.

14. The process according to claim 2, wherein the transanhydridation in step (c) is carried out in a continuously operated distillation column and the reaction products carboxylic acid (II) and carboxylic anhydride (VII) formed are continuously taken off.

15. The process according to claim 3, wherein the transanhydridation in step (c) is carried out in a continuously operated distillation column and the reaction products carboxylic acid (II) and carboxylic anhydride (VII) formed are continuously taken off.

16. The process according to claim 4, wherein the transanhydridation in step (c) is carried out in a continuously operated distillation column and the reaction products carboxylic acid (II) and carboxylic anhydride (VII) formed are continuously taken off.

17. The process according to claim 5, wherein the transanhydridation in step (c) is carried out in a continuously operated distillation column and the reaction products carboxylic acid (II) and carboxylic anhydride (VII) formed are continuously taken off.

18. The process according to claim 2, wherein the carboxylic acid (II) used is acetic acid.

19. The process according to claim 3, wherein the carboxylic acid (II) used is acetic acid.

20. The process according to claim 4, wherein the carboxylic acid (II) used is acetic acid.

* * * * *